United States Patent
Marshall, Jr. et al.

(10) Patent No.: US 7,166,752 B2
(45) Date of Patent: Jan. 23, 2007

(54) DECOMPOSITION OF CUMENE OXIDATION PRODUCT

(75) Inventors: Bernard K. Marshall, Jr., Kenova, WV (US); Anthony J. DeCaria, Murraysville, PA (US); Richard R. Hertzog, Morristown, NJ (US); Stylianos Sifniades, Ringwood, NJ (US); William B. Fisher, Chester, VA (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 997 days.

(21) Appl. No.: 10/199,770

(22) Filed: Jul. 19, 2002

(65) Prior Publication Data

US 2003/0088129 A1    May 8, 2003

Related U.S. Application Data

(63) Continuation-in-part of application No. 09/865,190, filed on Jul. 23, 2001, which is a continuation of application No. 08/601,879, filed on Feb. 15, 1996, now abandoned, which is a continuation of application No. 08/333,929, filed on Nov. 3, 1994, now abandoned, which is a continuation of application No. 08/203,845, filed on Feb. 28, 1994, now abandoned, which is a continuation of application No. 07/920,811, filed on Jul. 24, 1992, now abandoned, which is a continuation of application No. 07/297,333, filed on Jan. 17, 1989, now abandoned.

(51) Int. Cl.
C07C 45/42 (2006.01)
C07C 37/08 (2006.01)

(52) U.S. Cl. .................. 568/383; 568/385; 568/768

(58) Field of Classification Search .................. None
See application file for complete search history.

(56) References Cited

U.S. PATENT DOCUMENTS

| | | | |
|---|---|---|---|
| 2,663,735 A | 12/1953 | Filar et al. | |
| 2,757,209 A | 7/1956 | Joris | |
| 2,904,592 A | 9/1959 | Ellis et al. | |
| 2,957,921 A | 10/1960 | Adams et al. | |
| 3,271,457 A | 9/1966 | Bewley et al. | |
| 4,207,264 A | 6/1980 | Anderson et al. | |
| 4,209,465 A | 6/1980 | Austin et al. | |
| 4,210,606 A | 7/1980 | Austin et al. | |
| 4,210,607 A | 7/1980 | Austin et al. | |
| 4,238,417 A | 12/1980 | Austin et al. | |
| 4,246,203 A | 1/1981 | Wirth | |
| 4,267,379 A | 5/1981 | Austin et al. | |
| 4,283,567 A | 8/1981 | Nambu et al. | |
| 4,297,518 A | 10/1981 | Wu et al. | |
| 4,310,712 A | 1/1982 | Langley | |
| 4,358,618 A | 11/1982 | Sifniades et al. | |
| 5,254,751 A | 10/1993 | Zakoshansky | |
| 5,463,136 A | 10/1995 | Blackbourn et al. | 568/385 |
| 6,057,483 A | 5/2000 | Zakoshansky et al. | |
| 2002/0040165 A1 | 4/2002 | Hertzog et al. | 568/383 |

FOREIGN PATENT DOCUMENTS

EP    0 752 405 A    1/1997

OTHER PUBLICATIONS

"Chemie Ingenieur Technik" vol. 36. 1964/No. 7, Jul. by Carl V. Bertsche, pp. 2-39.
"A private report by the Process Economics Program", Stanford Research Institute, by Yen-Chen Yen, Apr. 1967, pp. 47, 53-60, 71-76, 311-323, drawing pp. 61, 63, 65, 67, 69.
"LA Chimicae L'Industria", vol. 65 Gennaio 1983, pp. 10-17.
"Journal of Applied Chemistry of the USSR" (Translated from Russian), pp. 225-227, 1968.
British Patent Specification 1202687, "Process for Preparing Phenol and Acetone", pp. 2-3, 1970.
"Hydrocarbon Processing, A Special Report-Maintenance in the HPI", Feb. 5, 1976, pp. 185-190, 193-196.
"Chemical Reaction Engineering", John Wiley & Sons, Inc., pp. 97, 98, 107, 108, 1962.

(Continued)

*Primary Examiner*—Sikarl A. Witherspoon
(74) *Attorney, Agent, or Firm*—Robert A. Koons, Jr.; Matthew P. McWilliams; Drinker Biddle & Reath LLP

(57) ABSTRACT

A process for decomposing a cumene oxidation product mixture containing cumene hydroperoxide (CHP) and dimethylphenyl carbinol (DMPC) to produce phenol, acetone and alpha-methyl styrene (AMS) with enhanced safety of operation and reduced by-product formation which comprises the steps: mixing the cumene oxidation product in a stirred or back-mixed reactor with an acid catalyst, with 10 to 100 percent acetone relative to the amount of acetone produced during the decomposition reaction, and with up to 4 weight percent additional amounts of water relative to the reaction mixture, at an average temperature between about 50° C. and about 90° C. for a time sufficient to lower the average CHP concentration of the reactor to between about 0.2 and about 3.0 weight percent, and wherein a portion of DMPC is converted to dicumyl peroxide (DCP); then reacting the reaction mixture from step (a) at a temperature between about 120° C. and 150° C. under plug-flow conditions for a time sufficient to decompose substantially all residual CHP and at least 90 percent of the DCP formed in step (a).

34 Claims, 3 Drawing Sheets

OTHER PUBLICATIONS

"Perry's Chemical Engineers' Handbook Sixth Edition" by Robert H. Perry, Don W. Green and James O. Maloney, pp. 13-19 and 13-25, 1984.

"CRC Handbook of Chemistry and Physics", by Robert C. Weast, Ph.D., Melvin J. Astle, Ph.D. and William H. Beyer, Ph.D., pp. C-72, C-244, C429, C-522, 1984-1985.

"Formation of Dicumyl Peroxide—A By-Product of the Process of Acid Catalytic Decomposition of Cumene Hydroperoxide" (Translated), by V.M. Zakoshanskii, pp. 1122-1126, 1989.

"Chemical Reaction Engineering", An Introduction to The Design of Chemical Reactors, John Wiley and Sons, Inc., pp. 94-119, 124-149, 308-329, 426, 427, 446-453, 1962.

"Chemical Reaction Engineering", Second Edition, John Wiley & Sons, pp. 100-103, 144-149, 218-229, 486, 487, 570-578, 1962.

Authorship Certificate 1699135, pp. 135.1-135.10, 1991.

Authorship Certificate 1563181, pp. 2-8, 1991.

Authorship Certificate 1391030, pp. 2-9, 1991.

Authorship Certificate 1361937, 1985.

Authorship Certificate III6688, pp. 2-8, 1984.

"Present State and Ways to Intensify Production of Phenol and Acetone by the Cumene Method", by V. M. Zakoskanskii, pp. 0-16, 1-8, 1988.

DECOMPOSITION OF CUMENE OXIDATION PRODUCT

This application is a continuation in part of co-pending U.S. application Ser. No. 09/865,190, filed on Jul. 23, 2001, which is a continuation of co-pending U.S. application Ser. No. 08/601,879, filed on Feb. 15, 1996, now abandoned which is a continuation of U.S. application Ser. No. 08/333,929, filed on Nov. 3, 1994, now abandoned, which was a continuation of U.S. application Ser. No. 08/203,845, filed on Feb. 28, 1994, now abandoned, which was a continuation of U.S. application Ser. No. 07/920,811, filed on Jul. 24, 1992, now abandoned, which was a continuation of U.S. application Ser. No. 07/297,333, filed on Jan. 17, 1989, now abandoned.

FIELD OF THE INVENTION

This invention relates to a process for the preparation of phenol wherein relatively high yields of alpha-methylstyrene (AMS), a useful by-product, are obtained.

BACKGROUND OF THE INVENTION

Phenol is manufactured via air oxidation of cumene to cumene hydroperoxide (CHP), followed by acid-catalyzed cleavage of CHP to phenol and acetone. CHP decomposition is a very exothermic reaction which is normally carried out on a commercial scale in continuous stirred or back-mixed reactors. In such reactors only a small fraction of CHP remains at any given time and the reaction medium consists essentially of the products of decomposition of CHP, i.e., phenol and acetone, plus any solvent (e.g., cumene) and other materials added with CHP to the reactor. During cumene oxidation small amounts of dimethyl phenyl carbinol (DMPC) and acetophenone are also formed. In the presence of acid catalyst, DMPC dehydrates to AMS, a useful by-product. Very high yields of AMS can be obtained from pure DMPC, e.g., 98 percent yield upon dehydration over acidic silica at 300° C. In the presence of phenol, however, and more specifically in phenol/acetone/cumene which is solvent in decomposition of technical CHP/DMPC mixtures, the AMS yield is normally about 50–60 mol percent of the DMPC. Main by-products are AMS dimers and cumylphenol which have no commercial value. Formation of cumylphenol also reduces the phenol yield.

G. G. Joris, U.S. Pat. No. 2,757,209, teaches that the amount of AMS dimers and cumylphenol formed can be substantially reduced by carrying out the reaction in two stages. In the first stage CHP is decomposed in a stirred or back-mixed reactor in the presence of small amounts of sulfur dioxide as catalyst and water as catalyst moderator. Preferred conditions are: temperature 45–65° C. sulfur dioxide 50–500 ppm, water 2–5 weight percent. Under these conditions the CHP concentration in the reaction mixture withdrawn from the reactor is less than 5 percent but more than 1 percent by weight. In the second stage, the mixture withdrawn from the first reactor is heated in a second reactor, optionally with additional catalyst, in order to decompose residual CHP and to effect the dehydration of DMPC to AMS. This second reactor is either a batch reactor, or a continuous plug-flow reactor. Preferred conditions are: temperature 110–120° C., reaction time 5–15 minutes. Care must be taken to stop the high temperature reaction once AMS formation is completed so as to minimize dimerization of AMS or the reaction of AMS with phenol to form by-products.

U.S. Pat. No. 4,358,618, to Sifniades et al. teaches that the amount of AMS dimers and cumylphenol formed is minimized by carrying out CHP decomposition in three stages. In the first stage, CHP concentration is reduced to 0.5–5 weight percent and DMPC is converted to dicumyl peroxide (DCP) to the extent of at least 40 mol percent. The reaction is carried out in a stirred or back-mixed reactor. Preferred conditions are: temperature 50–90° C., water 0.4–4.5 weight percent, acid 50–75 ppm. In the second stage, CHP concentration is reduced to below 0.4 weight percent by passage of the reaction mixture through a plug-flow reactor essentially isothermal to the first stage. In the third stage, both DCP and the remaining DMPC and CHP are decomposed by heating the reaction mixture to 120–150° C. in a plug-flow reactor.

In both the aforementioned patents a key element is the presence of relatively large concentrations of residual CHP in the first stage reactor. In fact we have found that the ultimate yield of AMS from DMPC in the three stage process of U.S. Pat. No. 4,358,618 generally increases as the concentration of residual CHP in the first step is increased. Unfortunately, the higher the concentration of CHP in a stirred or back-mixed reactor, the less stable is the operation of the reactor, particularly in a large scale reactor. This is due to the fact that CHP decomposition is highly exothermic, and at the same time it is accelerated by increasing temperature. Consequently, when a relatively large concentration of residual CHP is present, the opportunity exists for a large release of thermal energy if the reaction is accelerated by a hot spot, a local surge of catalyst or other ill-controlled events. In typical commercial back-mixed reactors stable operation is very difficult to achieve at average residual CHP concentrations greater than 2–3 weight percent.

British Patent 1,202,687, to Societa' Italiana Resine S.P.A. teaches that formation of cumyl phenol and other undesirable condensates can be suppressed by carrying out CHP decomposition at 300 to 70° C. with acetone and an aqueous solution of sulfuric acid of concentration 10 to 75 weight percent resulting in a reaction product that contains 37 to 48 weight percent of acetone and 0.05 to 1.0 weight percent of sulfuric acid. The reaction is carried out in a single stage. We have found that under the broad conditions specified by said patent it is possible to obtain a reaction product that contains significant amounts of residual CHP. This is the case, for example, if the reaction is carried out at 30° C. with 10% aqueous sulfuric acid, and the resulting reaction product contains 0.5 weight percent sulfuric acid and 48 weight percent acetone. It will be appreciated, however, that mixtures containing highly reactive compounds such as CHP are not appropriate for subsequent isolation of reaction products by conventional procedures such as distillation. It is clearly the intent of said patent to effect substantially complete decomposition of CHP before product isolation. We have found that when all CHP is decomposed in a single stage within the operating conditions specified by said patent, significant amounts of cumyl phenol and AMS dimers are formed. Moreover, some DCP is also formed which in the absence of a second stage designed to decompose DCP, further decreases the yields of useful products. If operating conditions are modified towards the regime of lower reactivity (e.g. less acid, lower temperature) in an effort to suppress formation of cumyl phenol and AMS dimers, the rate of DCP formation increases. Thus the process taught in said patent cannot be used to increase the yield of useful product beyond a certain point.

SUMMARY OF THE INVENTION

The present invention is concerned with the decomposition of cumene oxidation product in high yield to phenol, acetone and AMS, and particularly with the means of effecting such decomposition in a relatively stable and economical manner.

By adding acetone to the cumene oxidation product reaction mixture, in addition to acetone normally produced by the decomposition of CHP, relatively high yields of AMS are obtained even with residual CHP as low as 0.2 weight percent. The additional acetone may most conveniently be obtained by adiabatic flash evaporation of crude product downstream of the process. In this way the heat content of the crude product is utilized to produce the recycle acetone and energy savings are achieved. The additional acetone may also be obtained by refluxing an overhead vapor produced in the first stage reactor or series of reactors. The acetone obtained in these manners may also contain significant amounts of water.

An embodiment of the present invention includes a process for decomposing a cumene oxidation product mixture containing CHP and DMPC to produce phenol, acetone and AMS with enhanced safety of operation and reduced by-product formation which comprises the steps:

(a) mixing the cumene oxidation product in a first reactor (e.g. a stirred or back-mixed reactor) with an acid catalyst, with 10 to 100 percent acetone relative to the amount of acetone produced during the reaction and with an effective amount of water, at an average temperature between about 50° C. and about 90° C. for a time sufficient to lower the average CHP concentration of the reactor to between about 0.2 and about 3.0 weight percent and wherein a portion of DMPC is converted to DCP; then.

(b) reacting the reaction mixture from step (a) at a temperature between about 120 and 150° C. under plug-flow conditions for a time sufficient to decompose substantially all residual CHP and at least 90% of DCP formed in step (a).

In a preferred process, the product from step (b) is submitted to adiabatic flash evaporation, recovering an acetone-rich distillate which is recycled to step (a) to provide said acetone. In a preferred process, an acetone rich vapor from the cumene oxidation product reaction mixture from step (a) is condensed at a condenser or heat exchanger to provide said acetone. In a preferred process, the effective amount of water is an amount up to about 10 wt % of the reaction mixture. In a preferred process, the effective amount of water is up to about 4 wt % of the reaction mixture In one embodiment, step (a) additionally comprises reacting the reaction mixture having an average CHP concentration of between about 0.2 and about 3.0 weight percent at between 50° C. and about 90° C. under plug-flow conditions for a time sufficient to produce a reaction mixture having a CHP concentration no greater than about 0.4 weight percent.

In one embodiment, the invention includes a method for controlling variables in the reactor or series of reactors to eliminate or dampen fluctuations in the process operating conditions. These variables include residence time, temperature, acetone and water content. In one embodiment, automated controls are implemented for residence time and the first reactor content. In one embodiment, the method includes:

providing an excess amount of acetone in the reaction mixture in the first reactor;

monitoring the content of an acetone addition stream;

adjusting the feed rate of at least one of said inlet streams to offset fluctuations in the content of said acetone stream; and controlling the residence time of the first reactor.

In one embodiment of the invention, the method includes reacting the reaction mixture in a first reactor (or series of reactors) to decompose the CHP in the cumene oxidation product to phenol and acetone, and convert the DMPC in the cumene oxidation product to DCP, and in a second reactor, having plug flow conditions and elevated temperatures relative to the first reactor, convert the DCP formed in the first reactor into AMS and water. Also, the method includes adding excess acetone to the reaction mixture from about 10 to 100% excess acetone relative to the amount of acetone produced during the decomposition reaction, and optionally, water in an adjustable feed stream. The embodiment also includes monitoring the content of the acetone added to the reaction mixture, and adjusting the amount of water added to the reaction mixture based on the content of the acetone in order to maintain a substantially constant amount of water and acetone in the first reactor or series of reactors.

In one embodiment, the acetone solution is provided by recycling acetone within the phenol plant, e.g. by recovering the acetone solution from a crude product stream following the decomposition of DCP to AMS or other effluent stream. In one embodiment, an acetone solution is recovered and recycled from an effluent stream to the first reactor. In one embodiment, the average temperature in the first reactor (or series of reactors) is between about 50° C. and 90° C. and said average temperature in the plug-flow reactor for dehydrating the DCP is greater than said average temperature in the first reactor, provided that the second average temperature does not exceed 150° C.

In one embodiment, acetone is obtained by refluxing an acetone rich vapor in the first stage reactor or series of reactors. In one embodiment, the step of refluxing the acetone includes cooling the acetone rich vapor into an acetone containing mixture, collecting the acetone containing mixture in a vessel, and returning the acetone containing mixture to the cumene oxidation product reaction mixture. In one embodiment, the method includes automatically adjusting the amount of additional water added to the reaction mixture to dampen fluctuations in the mass composition of water in the recycle acetone added to the reaction mixture from the down-stream distillation area. This recycle acetone is added such that the amount of excess acetone is established and maintained in the reaction mixture at a substantially constant amount between about 10% to 100% acetone above the amount of acetone produced during the decomposition reaction.

In one embodiment, the level of reaction mixture in a first stage cleavage reactor or series of reactors is allowed to fluctuate in order to control the residence time in the reactor or series of reactors. In one embodiment, the method includes controlling the concentration of CHP and DCP in the reaction mixture and controlling the residence time in the reactors. In one embodiment, the standard deviation of the rise in temperature following acid addition to a slipstream, referred to herein as d(T) is less than 1.5. In one embodiment, this standard deviation is reduced to less than about 0.5.

DETAILED DESCRIPTION OF THE INVENTION

Figure 1:
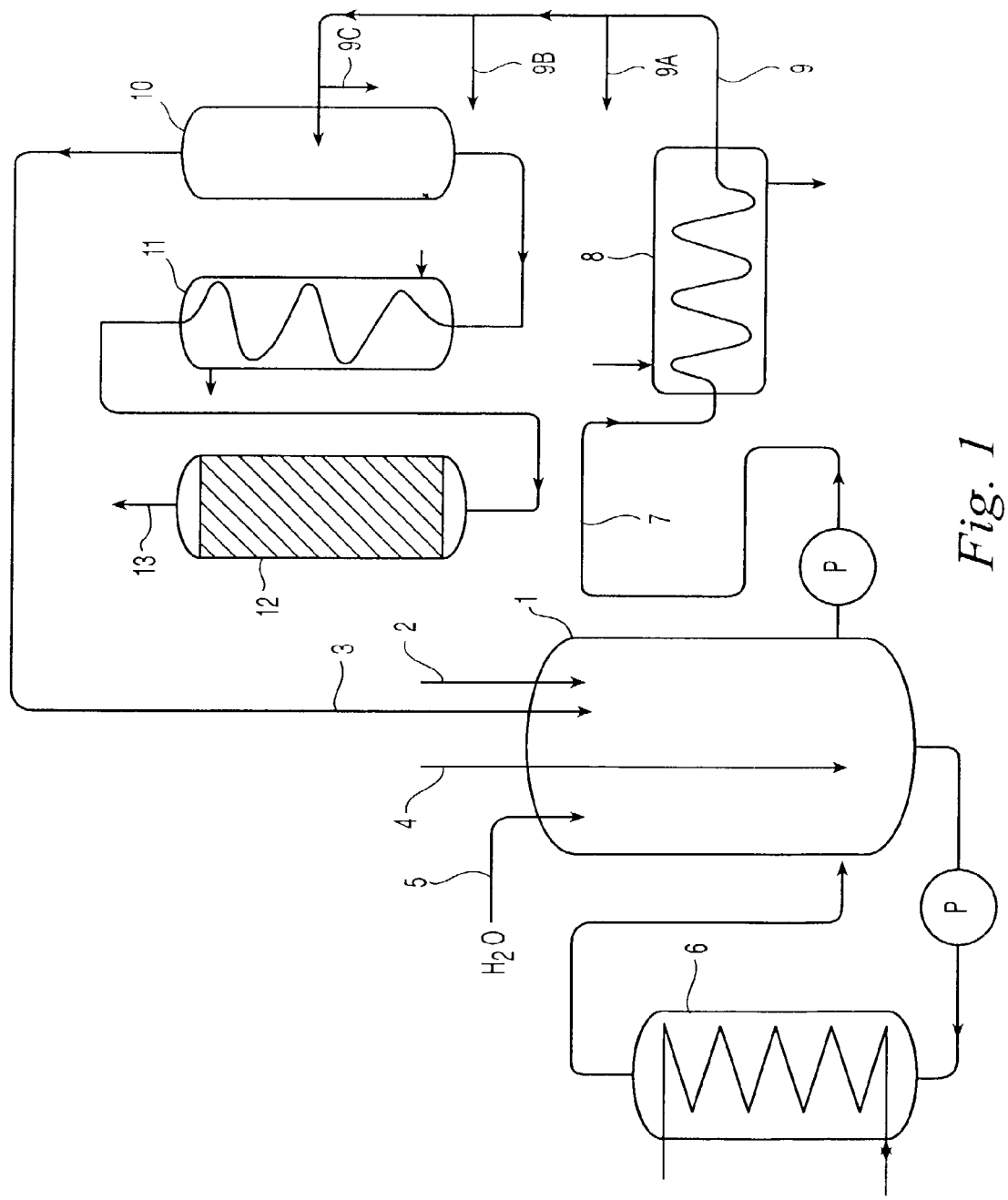
FIG. 1 shows a schematic arrangement of first example of equipment useful in practicing the process of this invention which includes a recycle acetone stream.

The method and process of the invention comprises the following steps.

In a first step (step (a)), cumene oxidation product is mixed with an acid catalyst, with acetone and optionally with a small quantity of water in a first cleavage or decomposition reactor, typically a stirred or back-mixed reactor, and is held for a sufficient time to reduce the average CHP content of the reactor to between about 0.2 and about 3.0 wt percent.

In a second step (step (b)), the effluent from step (a), is reacted at an elevated temperature, preferably between about 120 and 150° C. for a sufficient time in a plug-flow reactor to complete the decomposition to phenol, acetone and AMS.

In a third, optional step, the acetone is collected from the effluent from step (b), preferably by submitting the effluent to an evaporation step, more preferably an adiabatic flash evaporation, to produce an acetone-rich distillate. This distillate is then recycled to the reactor of step (a). It may be preferred that in step (a), the effluent from the first reactor is also held in a plug-flow reactor for a sufficient time to reduce the CHP content to below 0.4 weight percent before proceeding with step (b). In these embodiments, the decomposition or cleavage of CHP to phenol and acetone takes place in a series of reactors, e.g. stirred reactors, back-mixed reactors, or plug flow reactors, isothermal or at differing temperatures relative to the first reactor in the series.

The acid catalyst used in the process is selected from the group comprising sulfur dioxide, strong inorganic acids such as sulfuric, perchloric and the like, strong organic acids such as toluene sulfonic acid, and Lewis acids such as boron trifluoride or aluminum chloride. Typical acid catalyst levels are between 30 and 500 ppm (0.003–0.050 weight percent) of the reaction mass. Preferred catalysts include sulfuric acid and sulfur dioxide. It is believed that the acetone, or acetone and water solution, reduce the strength of the acidic catalyst and moderate the reaction, either by dilution/phase separation, as a Lewis base, or both. However, no assertion of or reliance upon these theories is made herein as underlying the improved reaction specificity.

The acetone used in the process may come from any convenient source, and may contain varying amounts of water. A preferred source is the acetone already produced in phenol producing plants, e.g. from the adiabatic flash-evaporation of the effluent from step (b). Additionally, flash evaporation of this effluent cools the flash residue. Since this effluent stream must normally be cooled before neutralization of the acid catalyst, the cooling caused by flash evaporation also reduces cooling expenditures that would be otherwise required in the production process. Additional sources for recycled acetone produced in phenol plants includes the acetone rich vapor from the overhead of the first reactor (or series of reactors) for decomposing CHP, or acetone obtained in distillation or waste streams. Evaporation of the reaction mixture helps cool the reaction and control the reactor temperature. Given and the relatively high volatility of acetone, the vapor typically contains a relatively high concentration of acetone and may be condensed and returned to the reaction mixture.

It is recognized that these exemplar sources may be used to increase the amount of acetone in the reaction mixture above that produced by the reaction itself, and may save energy that would be otherwise required to cool the reaction mixture or evaporate the added acetone. It is also recognized that these sources may be used alone or in combination.

The amount of acetone added to the reaction mixture is from about 10 percent to about 100 percent of the amount produced during the reaction. In the decomposition of a typical cumene oxidation product that contains 80 weight percent CHP, the recycled acetone corresponds from about 3 to about 30 weight percent of the oxidation product. Amounts less than 10 percent of that produced during the reaction have no significant beneficial effect on the reaction. Amounts higher than 100 percent are economically unattractive.

Water is also normally produced during the process in the dehydration and condensation reactions of DMPC. Additional amounts of water are introduced with the recycled acetone, especially if it is obtained by flash evaporation of the product of the second stage decomposition, plug-flow reactor. Acetone thus produced may contain from about 1 to about 5 weight percent of water. Normally, the water produced in the reaction and that introduced with the acetone is sufficient to moderate the activity of the acid catalyst. Preferably, small additional amounts of water may be added to further moderate the activity of the catalyst, and most preferably in a controlled amount to offset fluctuations in the amount of water introduced with the acetone. This is accomplished by monitoring the content of the acetone stream, and adjusting the feed rate of the water stream accordingly to maintain a substantially constant addition of water and acetone to the reaction mixture in the first reactor or series of reactors. The total amount of added water should not exceed about 4 weight percent of the reaction mixture. Too much water may cause the catalyst to become less active and slow down the reaction.

The average temperature in step (a) is from about 50° C. to about 90° C. The temperature may be maintained either by means of heat exchangers or by means of evaporative cooling. In the latter case the pressure of the reactor may be substantially below atmospheric so that the desired temperature may be achieved. When evaporative cooling is employed, acetone may preferably be obtained by condensing this vapor into an acetone rich solution and returning it to the reaction mixture. The residence time is from about 5 minutes to 2 hours. It will be appreciated that the operational objective is to maintain the average CHP concentration in the first reactor from between about 0.2 weight percent to about 3 wt percent. This can be achieved by an almost infinite variety of reaction conditions within the limits herein prescribed keeping in mind the following:

(a) Increasing the concentration of the acid catalyst, the temperature of the reactor and the residence time decreases the concentration of CHP.

(b) Increasing the concentration of acetone and the concentration of water increases the concentration of CHP.

If step (a) is carried out in a well-stirred reactor, both the temperature and the CHP concentration at various points of the reactor vary little from their respective average values. In such a reactor it is sufficient to monitor these quantities at only one point. If, however, a back-mixed reactor is employed, there will exist gradients of temperature and CHP concentration the magnitude of which will depend on the reactor geometry and recirculation ratio. In such a reactor the average temperature and CHP concentration are defined as the temperature and concentration that would result if the reactor contents were to be instantly homogenized. To estimate the averages it may be necessary to monitor the temperature and the CHP concentration in more than one point. Monitoring CHP is essential to the success of this process. To achieve a stable and safe operation it is preferable to have on-line analysis for CHP. This can be accomplished, for example, by means of an automatic hydroperoxide titrator, or by measuring the temperature rise in a slip-stream off the reactor circulated over a strongly acidic ion exchange resin as taught in Japanese Patent 7,446,278 to Mitsui, or by any other means.

U.S. Pat. No. 4,358,618 teaches that before completing the reaction in step (b), it is desirable to ensure that the CHP content of the reaction mixture is below 0.4 weight percent. This is so, because heating CHP at the relatively high temperatures of step (b) causes a small increase in the formation of by-products. Further CHP decomposition is accomplished in step (a) by optional steps (d) which normally employs a tube with residence time of up to a few minutes. In the process of the present invention the CHP content of the effluent from step (a) may be below 0.4 weight percent. In that case step (d) is not needed. Even at high CHP levels, step (d) may be omitted as a separate piece of equipment because CHP largely decomposes during the heatup period in the heat exchanger which is part of step (b) and which may fulfill the function of step (d).

An embodiment of the invention using recycle acetone can be illustrated by reference to FIG. 1 which can be compared to FIG. 1 of U.S. Pat. No. 4,358,618. Step (a) is performed in back-mixed reactor 1 at between 50° C. and 90° C. under conditions establishing a residence time of 5–120 minutes. Technical CHP, acetone, acid catalyst and water are introduced to the reactor through inlets 2, 3, 4, 5 respectively. The desired temperature is maintained by means of circulation through cooler 6. Due to the strong exothermicity of CHP decomposition, the minimum residence time in reactor 1, which includes time spent in cooler 6, is determined by the design of the cooler and the nature of cooling fluid. A practical lower limit of approximately 5 minutes is imposed if the coolant is water. Lower residence may be achieved if a refrigeration system is employed. The upper limit of residence time depends on the temperature, the acid content, the acetone content and the water content of the reaction mixture. A residence time of approximately 120 minutes may be considered as the upper limit. Preferred residence time is between 10 and 60 minutes.

The product from reactor 1 is next pumped through tube 7 to heater 8. Optional step (d) of the reaction may be carried out in tube 7 which may have sufficient capacity to provide a residence time between 0.1 and 5 minutes. The temperature in tube 7 is approximately the same as in 1. No means for cooling is provided, because the only significant reaction taking place in this step is decomposition of residual CHP which has already been reduced to 0.2–3 percent level in step (a). In heater 8 the product is heated to 120–150° C. and then is pumped to flash evaporator 10 through insulated pipe 9. In heater 8 and pipe 9 step (b) is carried out, i.e. decomposition of DCP and dehydration of DMPC to AMP as well as complete decomposition of any residual CHP. The temperature at the exit of pipe 9 is normally somewhat higher than that at the exit of heat exchanger 8 due to these reactions. Best AMS yields are obtained if the residence time in heater 8 is relatively short (e.g. under 30 seconds) compared to that in pipe 9 (at least 30 additional seconds), because in that way most of the residual DMPC and DCP decompose at the higher temperature regime which favors AMS formation. Pipe 9 is fitted with sampling ports at the entrance 9A, at an intermediate point 9B and at the exit 9C, for monitoring DCP concentration. At the flash evaporator 10, step (c), the reaction product' is cooled by 10–60° C. It is further cooled to 30–50° C. by passage through cooler 11 and then sent to an anion exchange resin bed, 12, in order to neutralize the acid catalyst. The neutralized product is then sent through pipe 13 to a distillation train for fractionation and recovery of the various components. The acetone-rich overheads from the flash evaporator are recycled to the back-mixed reactor through inlet 3.

It has been found that methods of the present invention have the benefits of increasing the stability of the decomposition reaction and reducing the fluctuations in the yield of AMS experienced in the commercial production of phenol from cumene oxidation product. It is also believed that the present invention reduces much of the process instability in many commercial cumene oxidation product decomposition systems caused by ill-controlled events in the first decomposition reactor (or reactors) or their ancillary systems. Examples of these instabilities include localized high concentrations of the acid catalyst, bumping in the recycle or reflux acetone stream, fluctuations in the content of the reactor feed streams, and the like. This instability results in fluctuations in the rate of decomposition in the first reactor, which in turn results in fluctuations in the amount of residual CHP present in and DCP produced by these reactors. Current methods of operation for these systems monitor the temperatures of the reaction mixture at one or more points in the reactor(s), as well as the d(T) of the reaction mixture. These parameters are periodically monitored, and adjustments are made to control the decomposition reaction. However, these methods do not adequately control the reaction, and fluctuations in the concentration of CHP and DCP in the mixture result in the loss of AMS yield and an increase in the aforementioned byproducts. Moreover, in systems which re-circulate significant amounts of reaction mixture within one or more reactors, use evaporative cooling/reflux acetone, or recycle acetone within the reactor, these fluctuations in the concentration of CHP and DCP appear to create feedback through the system, leading to long term, unpredictable shifts in the average concentration of CHP and DCP, as measured by the d(T) value of the reaction mixture.

In light of these instabilities, phenol plants operators establish maximum amounts of CHP (and DCP) which may be contained in the reaction mixture sent to the dehydration reactor. Since the d(T) value is used to monitor CHP and DCP concentration, in order to prevent downstream damage to the plant systems, an upper limit is set for the d(T) of the reaction mixture. If this value is exceeded, plant operators may be required to implement remedial measures, e.g. increasing the reactor's residence time, increasing the acid concentration to above optimum levels, or even shutting down the reactor, thereby significantly reducing the plant's phenol, acetone, and AMS capacity. The operator's remedial measures may also have only a delayed effect upon the reaction. Typical lag times between implementation and impact upon dT vary from between 1 to 30 minutes. Regardless, an excess or a lack of CHP will reduce the yield of AMS, phenol and acetone.

Thus, in order to maintain a margin of safety, plant operators in practice must maintain the average CHP concentration and d(T) value, far enough below the maximum allowable level so that process instability can be detected in the d(T) value and countered without risking reactor shutdown or damage. This level must also be set to take into account the apparent lag between the instance of instability (which causes the rise or drop in d(T)), and its detection.

In statistical terms, the wide variance of the d(T) value, as seen by a standard deviation above 1, requires operators to set the reaction conditions in the first reactor(s) at below optimum d(T) for the reactor to prevent this variance from impinging upon or exceeding the maximum allowable level. In practice, this results in a reduction in AMS yield.

In addition, it has been found that commercial plants also operate with reactors having a set reactor level, where there is a constant total volume of reactants in the first reactor(s). Since process instability may require operators to adjust the feed rates of the streams feeding the first reactor, these instabilities have an additional impact upon the residence time of the reaction mixture in the first reactors, particularly in continuous and re-circulating systems. These variables include reaction mixture residence time in the first stage reactor or series of reactors, reactor temperature in the first stage reactor, and acetone and water concentration in the first stage reactor. By reducing or eliminating fluctuations in these variables, the process becomes more stable, and increases the amount of DCP available for conversion to AMS in the second stage reactor. This increase can be measured indirectly by the change in temperature, d(T), of a small side stream in a differential calorimeter upon the exhaustive addition of acid catalyst to a slipstream taken from the system, preferably from the first stage or plug flow reactor. The greater the residual amount of CHP and DCP, the greater the value for d(T).

Figure 3:
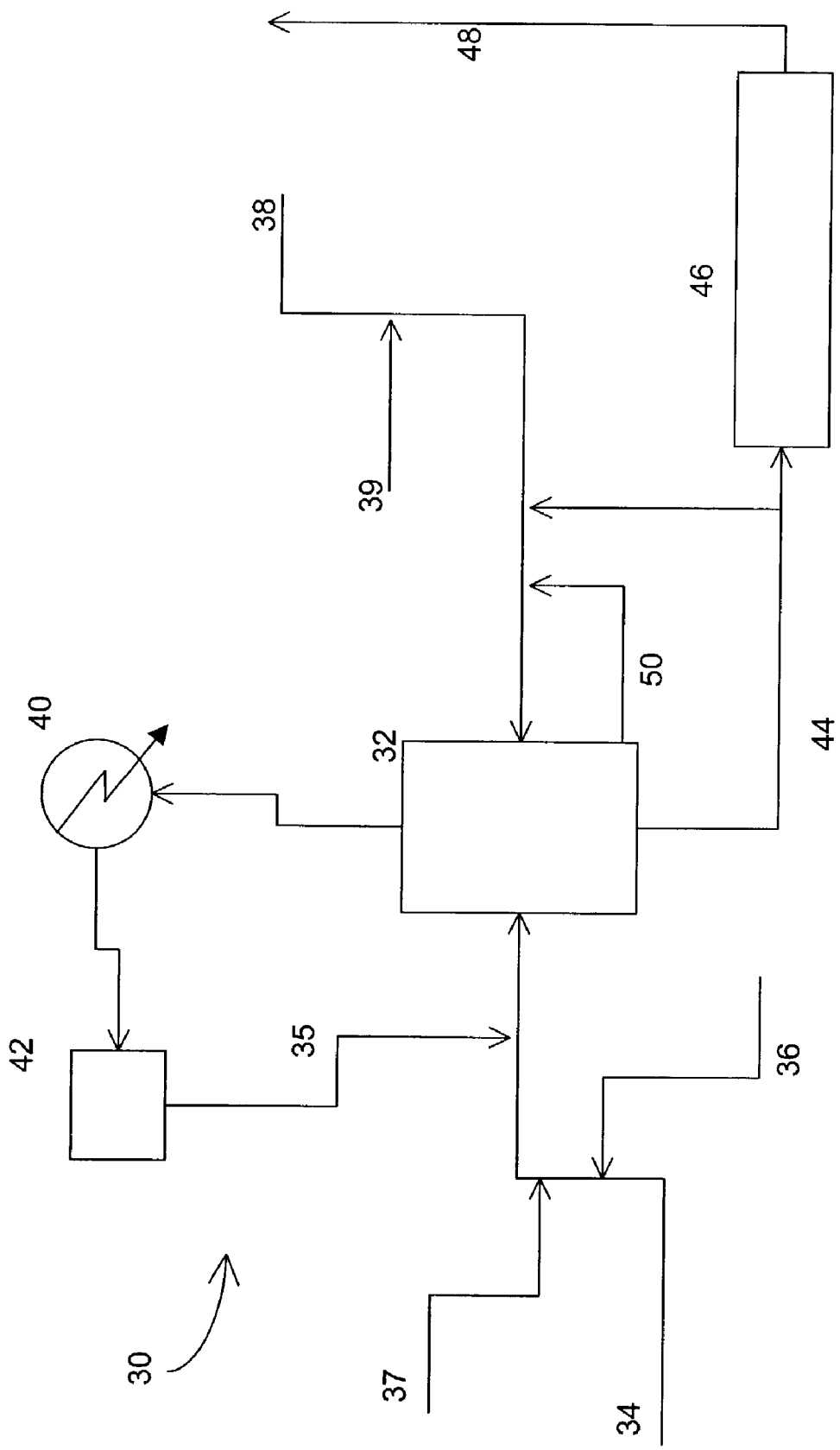
FIG. 3 depicts a simplified schematic diagram of a second example of the equipment used in practicing the process of the invention, including both a recycle acetone stream and a reflux acetone stream.

FIG. 3 depicts an apparatus according to the additional embodiment of the invention, including a stirred first stage cleavage reactor, a condenser for returning acetone to the first stage reactor, and a second stage dehydration reactor, e.g. a plug flow reactor. High variability in the yield of AMS from the dehydrator in this embodiment led to an investigation of the sources of process instability.

The range of variability in AMS yield spanned from a low of about 63 mol percent to a high of about 83 mol percent over the course of a three year period for two reactors having a design as depicted in FIG. 3, but with a set reactor level and without residence time controls. The yearly averages 75.2 mol %, 72.8 mol %, and 77.7 mol %. The sources for this variability were investigated, and found to be based primarily in fluctuations in the reaction mixture's content while in the first stage reactor.

Investigation of the process revealed high variability in d(T) value, in both short term d(T) values, e.g. variability in 1–3 minutes, and long term d(T) values, e.g. variability over 15–40 minutes. The long term variability appeared to be caused by fluctuations in the residence time and water concentration in the reactor. In particular, it was determined that the actual residence time for a reactant species (e.g. CHP, DMPC, DCP, etc.) varied due in substantial part to fluctuations in the amount of acetone and water in the first stage reactor. Control of the residence time was accomplished by allowing the liquid level of the first stage cleavage reactor (also referred to herein as the decomposer, or first reactor(s)) to fluctuate based upon the total feed rate to the reactor, albeit these fluctuations should of course be within the safety parameters of the individual reactor. Surprisingly, by allowing the reactor level to fluctuate, particularly in response to fluctuations and adjustments in the feed rate of cumene oxidation product, long term fluctuations in the residence time of the reaction mixture in the first stage reactor were essentially reduced to below the threshold for detection.

The invention may be further illustrated by means of the following examples.

EXAMPLE 1

A cumene oxidation product that contained 81.6 weight percent CHP, 5.00 weight percent DMPC and 0.40 weight percent acetophenone, the balance being mostly cumene, was pumped at the rate of 1.62 g/min into a thermostated pyrex Morton flask equipped with magnetic stirring and an overflow device that maintained the volume of the reaction mixture at 30 mL. Simultaneously, an acetone solution containing 0.86 weight percent AMS, 2.06 weight percent phenol, 5.83 weight percent cumene, 1.60 weight percent water and 0.0512 weight percent sulfuric acid was pumped into the reactor at the rate of 0.230 g/min. The composition of the acetone solution, except for the acid content, corresponded to that of a flash distillate that could be obtained from the product of the reaction. The acetone added was equivalent to approximately 40 percent of the acetone produced during the reaction. The acid content was calculated to maintain 80 ppm in the reaction mixture. The residence time in the reactor was 16 minutes and the temperature 80° C. The stirred reactor effluent was pumped through a ⅛" stainless steel tube reactor immersed in a bath at 125° C. The residence time in the tube was 1.6 minutes. After the two reactors had reached steady-state operation, samples were withdrawn for analysis at the exit of each reactor. Subsequently, the temperature of the bath in which the tube reactor was submerged was increased to 135° C. and again to 145° C.

Samples were withdrawn for analysis in each case after the system had attained steady-state. The effluent from the stirred reactor contained on the average 2.26 weight percent DCP and 0.51 weight percent residual CHP. The yield of AMS in that effluent was 47%. The yield of AMS in the effluent of the tube reactor was 75.1, 78.0 and 78.3 mol percent respectively at 125, 135 and 145° C. The yield of AMS was computed as follows:

$$\text{Yield} = 100 \times (AMS - AMS_O)/(CE - AMS_O)$$

where $AMS_O$ is the concentration of AMS in the charge and CE is the total carbinol equivalent which is defined as the sum of all products that can be formed by reactions of DMPC. The main components of CE are DMPC, AMS, DCP, AMS dimers and cumylphenol.

Other examples using substantially the same cumene oxidation product but variable reaction conditions are summarized in Table I. Examples 7 through 11 utilized no added acetone and they are shown for comparison purposes. In example 12 the acetone added corresponded to 60 percent acetone recycle but the sulfuric acid was increased to 0.500 pm and the residence time to 20 minutes so that the residual concentration of CHP in the stirred reactor effluent was substantially zero. DCP was 0.55 weight percent. The yield of AMS in the stirred reactor effluent was 62.6% and it increased to 68.1% after further reaction at 125° C. in a tube reactor. In some examples a post-reactor isothermal to the stirred reactor was also used. This was ⅛" stainless steel tube with residence time approximately 3 minutes.

Figure 2:
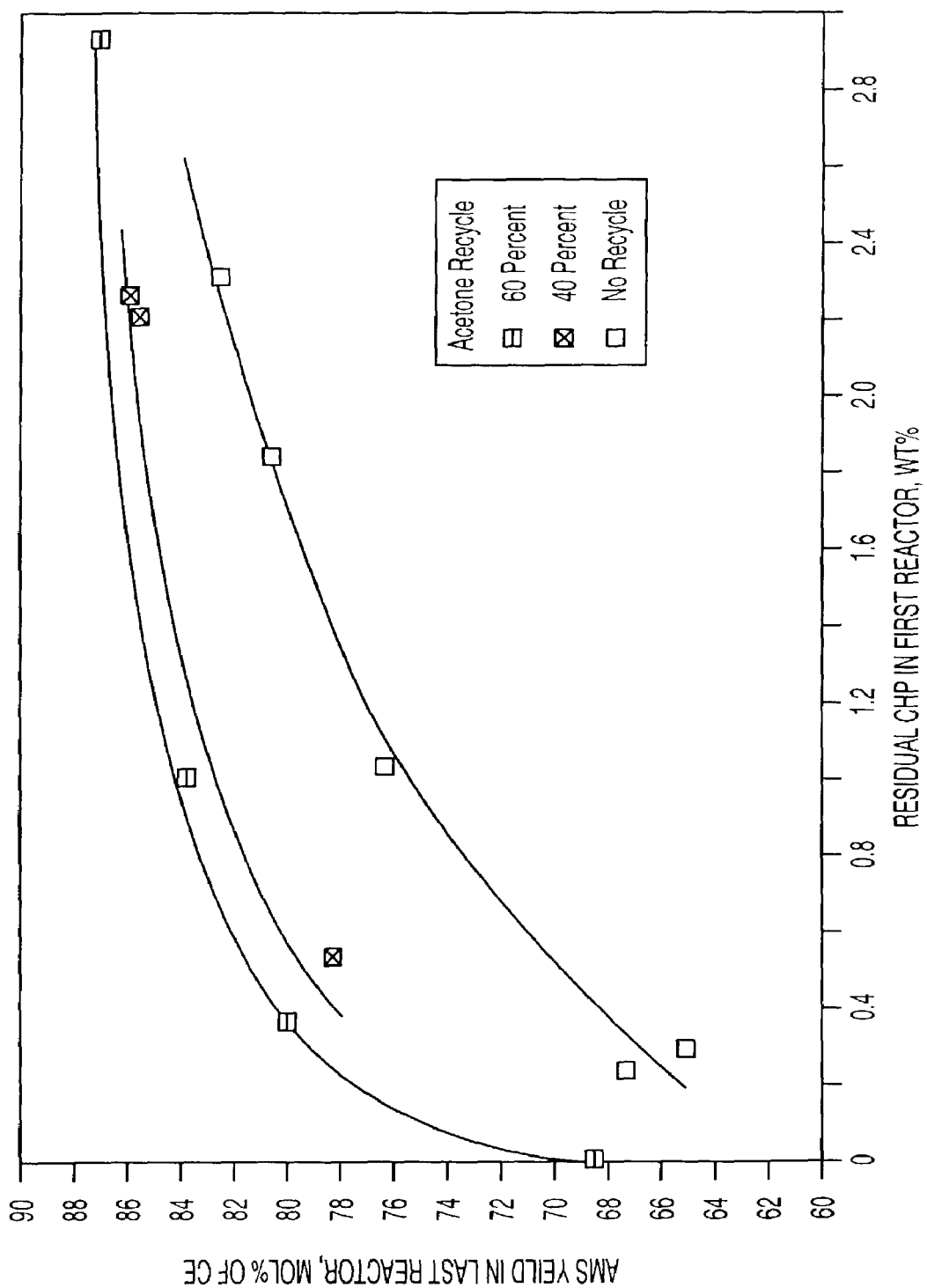
FIG. 2 provides AMS yield versus CHP concentration in the stirred reactor for 60 percent, 40 percent, and no acetone recycle.

The maximum yield of AMS obtained in these examples is plotted in FIG. 2 against the concentration of residual CHP in the stirred reactor. The lowest curve (open squares) represents examples with no recycled acetone. The middle curve (squares with an x) represents examples with 40 percent acetone recycle. The upper curve (solid squares) represents examples with 60 percent acetone recycle. It is clear from FIG. 1 that by recycling acetone to the stirred reactor it is possible to obtain good AMS yields and correspondingly low residue formation at a relatively low concentration of residual CHP. It is also clear that AMS yield falls off substantially if the concentration of residual CHP is reduced below 0.2 weight percent even when acetone is recycled to the stirred reactor.

TABLE 1

DECOMPOSITION OF CUMENE OXIDATION PRODUCT[1]

| EXAMPLE | ACETONE RECYCLE % | WATER ADDED % | STIRRED REACTOR | | |
|---|---|---|---|---|---|
| | | | TEMP ° C. | HP WT % | DCP WT % |
| 1 | 40 | 0.21 | 80 | 0.51 | 2.26 |
| 2 | 40 | 0.21 | 70 | 0.96 | 3.75 |
| 3 | 40 | 0.90 | 80 | 2.21 | 4.71 |
| 4 | 40 | 0.90 | 80 | 2.16 | 4.27 |
| 5 | 60 | 0.08 | 80 | 0.33 | 1.77 |
| 6 | 60 | 0.90 | 80 | 2.94 | 4.32 |
| 7 | 0 | 0.03 | 70 | 0.22 | 2.73 |
| 8 | 0 | 0.03 | 70 | 0.28 | 2.60 |
| 9 | 0 | 0.84 | 70 | 1.79 | 5.80 |
| 10 | 0 | 0.84 | 80 | 1.00 | 3.61 |
| 11 | 0 | 1.34 | 80 | 2.27 | 5.17 |
| 12 | 60 | 0.10 | 80 | 0.00 | 0.55 |

| EXAMPLE | POST REACTOR CHP, WT % | AMS YIELD PLUG FLOW TEMPERATURE, ° C. | | |
|---|---|---|---|---|
| | | 125 | 135 | 145 |
| 1 | — | 75.1 | 78.0 | 78.3 |
| 2 | — | 78.3 | 82.6 | 83.7 |
| 3 | — | 75.7 | 84.3 | 85.7 |
| 4 | 0.12 | 75.7 | 84.3 | 85.4 |
| 5 | 0.04 | 77.3 | 79.1 | 80.1 |
| 6 | 0.11 | 81.0 | 86.8 | 84.1 |
| 7 | 0.06 | 67.2 | 66.2 | 65.0 |
| 8 | — | — | 65.1 | — |
| 9 | — | 79.8 | 80.5 | 78.4 |
| 10 | — | 75.7 | 76.3 | 75.1 |
| 11 | 0.15 | 79.3 | 82.1 | 82.4 |
| 12 | — | 68.1 | — | — |

$H_2SO_4$ = 80 ppm, time = 16 min except in Example 12 which had 500 ppm and 20 min respectively.

EXAMPLE 2

FIG. 3 is a simplified schematic diagram of a decomposition of cumene oxidation product system 30. The system includes a first reactor 32 operating with an adjustable reactor level; a condenser 40 and reflux acetone collection vessel 42; and a second reactor 46 for DCP dehydration having plug flow conditions and an elevated temperature, which produces decomposition product mixture stream 48.

First reactor 32 is a continuously stirred, tank reactor, and is fed by cumene oxidation product stream 34, recycle acetone stream 35, sulfuric acid feed stream 38, and water feed stream 36. Water is added in an amount of up to about 10% by weight of the reaction mixture. Typical operating conditions for reactors of this design are depicted in Table 2 below, though these conditions can vary substantially from reactor to reactor depending on the processing plant's design and system tolerances. Otherwise, the reaction conditions in first reactor 32 are similar to those described in reference to FIG. 1.

TABLE 2

| Parameter | Low | Preferred | High |
|---|---|---|---|
| $H_2SO_4$ (ppm) | 250 | 350–375 | 650 |
| Water (wt. %) | 0.9 | 1.5 | 2.7 |
| technical CHP grade (wt. %) | 78 | 82–86 | 92 |
| Recycle Acetone (wt. % acetone actually produced) | 25 | 35 | 45 |
| Water Content of Recycle Acetone (wt. %) | 0.02 | 0.07–1.3 | 1.9 |
| First Stage Reactor Residence Time (min.) | 4 | 7 | 11 |
| Reflux Ratio (Reflux/CHP feed) | 2.1 | 2.4 | 3.1 |
| Temp. (1st Stage Reactor) (° C.) | 73.8 | 77.2 | 87.7 |
| dT (° C.) | 10 | maximum safe value | 12.2 |

In relevant part, first reactor 32 is a continuously stirred tank reactor having similar temperature, residence times and reaction mixture compositions as described in reactor 1, FIG. 1, although configured to operate using a boiling reaction mass. An acetone overhead vapor produced in first reactor 32 is cooled by condenser 40 and collected in reflux collection vessel 42. The predominantly acetone mixture is then allowed to run back into the reaction mixture. Typically, the reflux acetone collected contains 90–95% acetone, and 4 to 7% water, with the balance being organic reaction components of the reaction mixture.

The amount of CHP in the reaction mixture in reactor 32 is also monitored by online analysis of slipstream 50. In this example, slipstream 50 represents an extremely small amount of reaction mass. The temperature of the reaction mixture is measured initially after it is withdrawn from the reactor through slipstream 50, an excess amount of acid catalyst is then added to the slipstream, preferably using a mixing "T" or small vessel (not shown). The excess acid catalyst causes the exothermic decomposition of the residual CHP and the DCP present in the reaction mixture, causing a rise in temperature. The value dT represents the difference in temperature of the slipstream before and after acid addition. The system also included an automatic temperature alarm (not shown) set to initiate an automatic shutdown should the dT of reaction mixture exceed a maximum safe value. The maximum safe value in the system used was 22 to 26° F. (12.2° C. to 13.3° C.), however, this value can be higher or lower in other systems depending on a number of factors, including the system's configuration, condition and age. Following reactor 32, the reaction mixture is sent through pipe 42 to second reactor 46, with 10% of the reaction mixture being diverted to the acid feed mixing T to dilute the acid stream 38 prior to being fed to first reactor 32.

Second reactor 46 is maintained at an elevated temperature relative to first reactor 32, and produces crude product stream 48. An additional improvement to AMS yield was obtained by automating the control of key variables that influence the amount of DCP and residual CHP exiting the first stage reactor.

In this example, the acetone added to the reactor in recycle acetone stream 34 contains acetone recovered from effluent streams elsewhere in the phenol plant. Its content is monitored using automated online analysis, and the feed rate of the water addition stream is automatically adjusted to offset or dampen fluctuations in the content of the acetone stream.

The benefits of the present invention have been demonstrated comparison of the fluctuations in dT values in a test reactor before and after implementation of dampening controls and reactor level fluctuation. First, over a twenty day control test period without dampening controls and without residence time control, the dT value was seen to fluctuate abruptly from 6 to over 16 over both short and long term periods. During this control period, the process was operated using prior art methods, e.g., operators monitored dT, and, in response to fluctuations in dT, manually increased or decreased the reactor residence time or the feed rate of water. As seen in Table 3 below, significant amounts of process time were spent above or below the preferred amount for improved AMS yield. A five day period sample period was taken from this 20 day control period for statistical comparison to a five day test period in the same reactor. During the 5 day test period, residence time was controlled by allowing the reactor level to fluctuate, and the feed rate of the water addition stream was programmed using the system's DCS (GSE), primarily to adjust to control the dT at a given setpoint and secondarily to automatically adjust to compensate for fluctuations in the water content of the recycle acetone.

The fluctuations in reactor level were seen to reach as much as about 10% of the reaction mass, but typically fluctuations were seen to be between about 0 and 6%. Data were collected over the five day test period, also using DCS (GSE), and the results are summarized in Table 3 below.

TABLE 3

| Reactor Level Set | Controls Present | Period | Feed (gpm) | Process Stability | Avg. dT °C. | Low °C. | High °C. | Std. Dev. |
|---|---|---|---|---|---|---|---|---|
| No | No | 20 days | 135 | unstable | not measured | 6.0 | 16.3 | not measured |
| No | No | 5 days | 135 | unstable | 10.66 | 6.0 | 16.3 | 1.63 |
| Yes | Yes | 5 days | 129 | stable | 11.95 | 10.75 | 13.75 | 0.38 |

The standard deviation for the d(T) is reduced from 1.63 to 0.38, with an the average value of 11.95, and an increase in residence time from 6.5 to approximately 7.1 minutes. Also the corresponding average values for the water feed rate and residence time were monitored and recorded, and these results are summarized in Table 4 below.

TABLE 4

| Reactor Level Set | Controls Present | Period | Avg. dT | Water feed Rate | Residence Time |
|---|---|---|---|---|---|
| No | No | 20 days | not measured | 0 to 2.0 | 4 to 8 |
| No | No | 5 days | 10.66 | 1.33 | 6.66 |
| Yes | Yes | 5 days | 11.95 | 1.49 | 6.99 |

Upon implementation of the dampening controls and the residence time controls, the average water feed rate increased slightly from 1.33, and to 1.49, while the residence time increased from 6.66 and to 6.99. Using the set reactor level and control methods of the prior art, typically increasing water feed and increasing residence time are undertaken in response to a short term increase in dT, to cause a reduction in dT, and result in a corresponding reduction in AMS yield. In contrast, using the control methods described herein, the increase in process stability ensured that the process was operated safely, but with an increase in the average dT from 10.66 to almost 12, with an expected corresponding increase in AMS yield.

What is claimed:

1. A method for decomposing a cumene oxidation product containing cumene, cumene hydroperoxide (CHP) and dimethylphenyl carbinol (DMPC) to produce phenol, acetone and alpha-methyl styrene (AMS), comprising the steps of:

providing a first reaction mixture including
cumene oxidation product,
an acid catalyst,
an acetone solution, in an amount such that 10 to 100 percent acetone
relative to the amount of acetone produced during the decomposition
reaction is added to the reaction mixture, and optionally
water, said water being added in a stream having an adjustable feed rate;

reacting the reaction mixture in a first reactor at a first average temperature to produce phenol and acetone and wherein said DMPC is converted to dicumyl peroxide (DCP);

reacting the reaction mixture in a second reactor under plug-flow conditions at a second average temperature for a time sufficient to decompose the DCP into AMS and water to form a product mixture;

recovering said acetone solution from the product mixture;

recycling said acetone solution from the product mixture to the first reactor;

monitoring the content of the acetone solution by on-line analysis; and adjusting the feed rate of the water in response to the content of the acetone solution;

wherein said first average temperature is between about 50° C. and 90° C. and said second average temperature is greater than said first average temperature, provided that said second average temperature does not exceed 150° C.

2. The method of claim 1, further comprising allowing the level of reaction mixture in the first reactor to fluctuate.

3. The method of claim 1, further comprising refluxing an acetone rich overhead vapor produced by the CHP decomposition reaction in the first reactor.

4. The method of claim 1, wherein said first reactor comprises a series of reactors, provided that at least one reactor has plug flow conditions.

5. A method for producing phenol, acetone and AMS by the decomposition of cumene oxidation product with an acidic catalyst, the method generally having a first decomposition system having a first reactor, a set of inlet streams, said set of inlet streams including a recycle acetone stream, a water stream, and a cumene oxidation product feed stream, and a reaction mixture comprising phenol, acetone, DCP, and CHP, said reaction mixture being fed to a second decomposition system producing a product mixture comprising phenol, acetone, and AMS, comprising:

providing an excess amount of acetone in said reaction mixture;

monitoring the content of said recycle acetone stream;

adjusting the feed rate of at least one of said inlet streams to offset fluctuations in the content of the recycle acetone stream; and controlling the residence time of the first decomposition system.

6. The method of claim 5, further comprising the step of refluxing an acetone vapor in said first decomposition system.

7. The method of claim 5, wherein the average concentration of DCP in the reaction mixture is increased, while a standard deviation of said average concentration is decreased.

8. The method of claim 5, whereby long term fluctuations in the concentration of CHP and DCP in the reaction mixture are dampened to vary with a standard deviation of dT measured over a five day period of less than about 1.6.

9. The method of claim 5, whereby long term fluctuations in the concentration of CHP and DCP in the reaction mixture are dampened to vary with a standard deviation of dT measured over a five day period less than about 0.6.

10. The process of claim 6, further comprising the step of allowing the level of the first reactor to fluctuate.

11. The process of claim 8, wherein the feed rate of the water stream is adjusted to offset fluctuations in the content of the recycle acetone stream.

12. The process of claim 6, further comprising the step of allowing the level of the first reactor to fluctuate by about 15% relative to the average level of the reaction mixture.

13. The method of claim 12, wherein long term drift in the concentration of CHP and DCP in the reaction mixture is substantially eliminated.

14. A method for the decomposition of cumene hydroperoxide to phenol and acetone by the addition of acidic catalyst, having a series of reactors, a recycle acetone stream, a water addition stream, and a reaction mixture having excess acetone, comprising, refluxing acetone rich vapor in a reactor, monitoring the content of the recycle acetone stream, and automatically adjusting said water addition stream to dampen fluctuations in the mass composition of acetone and water within said recycle acetone stream, wherein said excess acetone is established and maintained in the reaction mixture at an amount between 10 to 100% wt. above the amount of acetone produced during the decomposition reaction.

15. The method of claim 14, further comprising allowing the level of the first reactor to fluctuate, and wherein the residence time of the cumene oxidation products in the first reactor is maintained at a steady state.

16. The method of claim 14, whereby long term fluctuations in the concentration of CHP and DCP in the reaction mixture are substantially eliminated.

17. An improved method for the decomposition of cumene oxidation product by the addition of acidic catalyst using a series of reactors, wherein the improvement comprises:

providing a reaction mixture with between 10 to 100% excess acetone relative to the amount of acetone produced in the decomposition of the cumene oxidation product;

maintaining a steady residence time for the cumene oxidation product within the series of reactors, and allowing the level of the first reactor to fluctuate.

18. The method of claim 17, wherein long term drift in the concentration of CHP and DCP in said series of reactor is substantially eliminated.

19. The method of claim 17, wherein said step of providing between 10 to 100% excess acetone comprises the steps of:

condensing an acetone rich vapor produced within in an overhead vapor in the series of reactors into a first acetone solution;

returning said first acetone solution to said series of reactors;

transferring the reaction mixture to a separate vessel subjecting the reaction mixture to a flash evaporation to produce a second acetone solution; and transferring said second acetone solution to the series of reactors.

20. The method of claim 19, whereby the average yield of AMS is increased.

21. The method of claim 19, wherein fluctuations in the ratio of acetone and water to phenol within the first reactor are dampened by adjusting the feed rate of water to the reactor.

22. The method of claim 19, wherein the acidic catalyst is selected from the group consisting of sulfuric acid, sulfur dioxide, boron trifluoride, toluene sulfonic acid, and aluminum chloride.

23. The method of claim 19, wherein the series of reactors comprises said first reactor, said first reactor having a first average temperature between about 50° C. and 90° C., a second reactor substantially isothermal to the first reactor, said second reactor having plug flow conditions, and a third reactor, said third reactor having plug flow conditions and a second average temperature greater than the average temperature of said first reactor, provided that said second average temperature does not exceed 150° C.

24. The method of claim 23, wherein said second average temperature is from about 120° C. to 150° C.

25. A method for increasing the selectivity of the decomposition of cumene oxidation product by acidic catalyst to phenol and acetone using a first reactor and at least a one plug flow reactor downstream from said first reactor, the at least one plug flow reactor having an elevated average temperature relative to the first reactor, comprising, decomposing cumene hydroperoxide in said first reactor in the presence of a substantially constant amount of water and excess acetone, said excess acetone being in an amount between 10 to 100% excess relative to the amount of acetone produced during the decomposition reaction;

wherein the residence time for CHP in the first reactor is maintained at a steady time and the level of the first reactor is allowed to fluctuate.

26. The method of claim 25, further comprising the steps of providing additional water to the reaction mixture in the first reactor, and controlling the mass percentage of water and acetone present in said first reactor.

27. An improved method for decomposing cumene oxidation product to AMS, phenol and acetone in a series of reactors, comprising:

providing an excess acetone in a reaction mixture by recycling acetone produced by decomposing cumene oxidation product to the reaction mixture, monitoring the content of said acetone using online analysis, whereby a signal is generated; and using said signal to automatically adjust a feed rate of additional water to the series of reactors; and allowing the level of reaction mixture in the series of reactors to fluctuate.

28. The improved method of claim 27, wherein the excess acetone is in an amount between 10% to 100% by weight of the amount acetone produced in the decomposition reaction.

29. The improved method of claim 28, wherein a cumene oxidation product, an acidic catalyst and the excess acetone are provided in a first reactor, and an acetone rich vapor is collected from said first reactor, condensed and returned to said first reactor.

30. The improved method of claim 27 wherein additional water is added to the cumene hydroperoxide decomposition products to a level not greater than 4 wt. % by of the reaction mixture.

31. The improved method of claim 29, wherein the level of the series of reactor is allowed to fluctuate relative to the average level of the first reactor.

32. The improved method in accordance with claim 31, wherein the level fluctuates by as much as about 10% over a five minute period relative to the average level of the first reactor.

33. The improved method in accordance with claim 27, further comprising the step of producing an acetone rich vapor a first reactor, condensing said acetone rich vapor, and allowing said condensate to return to said first reactor.

34. The method of claim 33, wherein the acetone rich vapor is condensed in a vessel separate from the first reactor.

* * * * *